United States Patent [19]

Luceri

[11] Patent Number: 4,654,040
[45] Date of Patent: Mar. 31, 1987

[54] SMOOTH-EDGED CONTOURED SANITARY NAPKIN

[75] Inventor: Thomas J. Luceri, Bridgewater, N.J.

[73] Assignee: Personal Products Company, Milltown, N.J.

[21] Appl. No.: 833,627

[22] Filed: Feb. 27, 1986

[51] Int. Cl.⁴ .......................................... A61F 13/16
[52] U.S. Cl. ................................. 604/385 R; 156/202
[58] Field of Search .................... 604/385.1, 386, 378, 604/389, 379, 380, 358; 156/202

[56] References Cited

U.S. PATENT DOCUMENTS

| 4,425,130 | 1/1984 | DesMarais | 604/385.1 |
| 4,560,379 | 12/1985 | Stemmler | 604/385.1 |
| 4,596,244 | 6/1986 | Jackson | 604/389 |

Primary Examiner—John D. Yasko
Attorney, Agent, or Firm—Jason Lipow

[57] ABSTRACT

A smooth edged, "C"-folded sanitary napkin is provided, there being a tuck in each longitudinal edge so as to produce a body contoured product.

19 Claims, 10 Drawing Figures

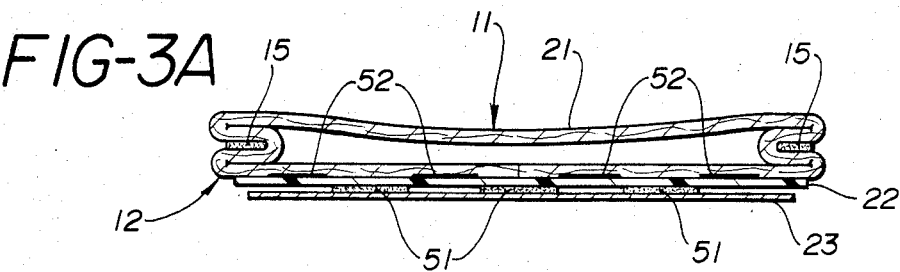
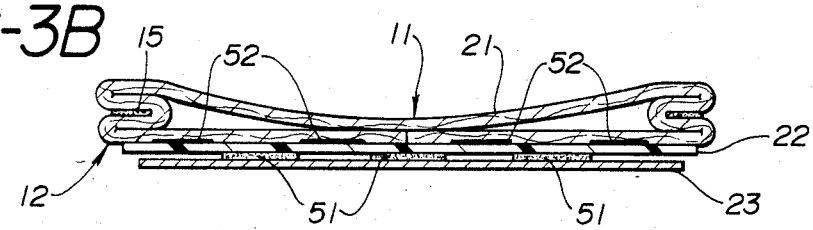
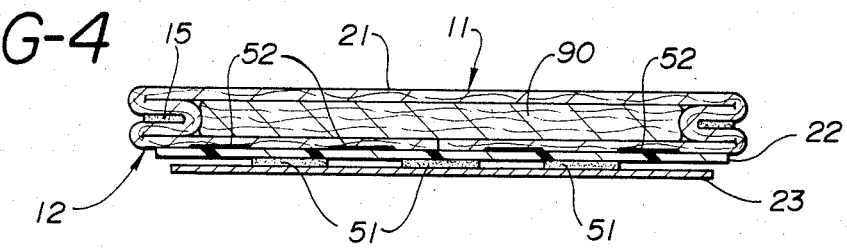
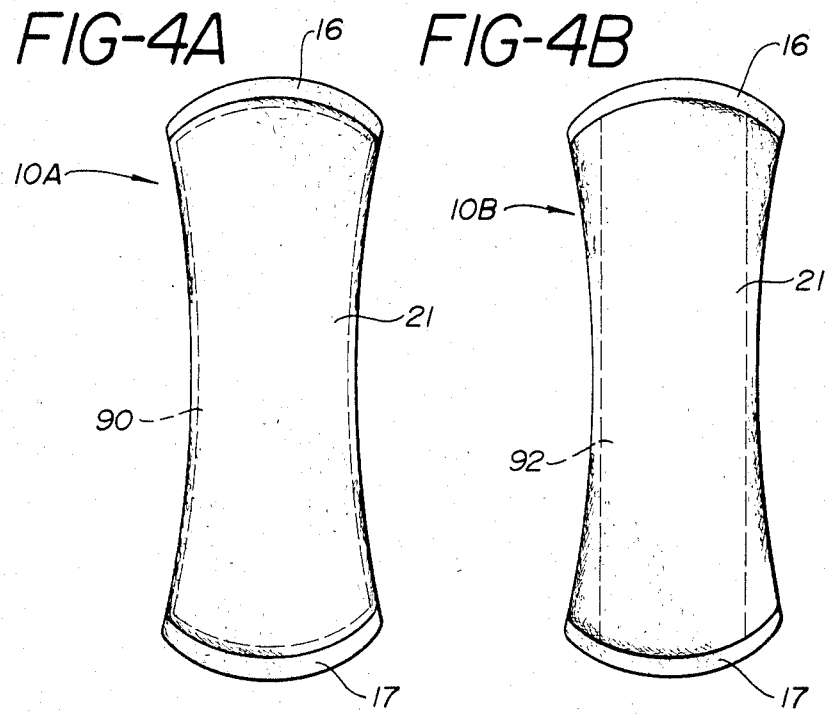

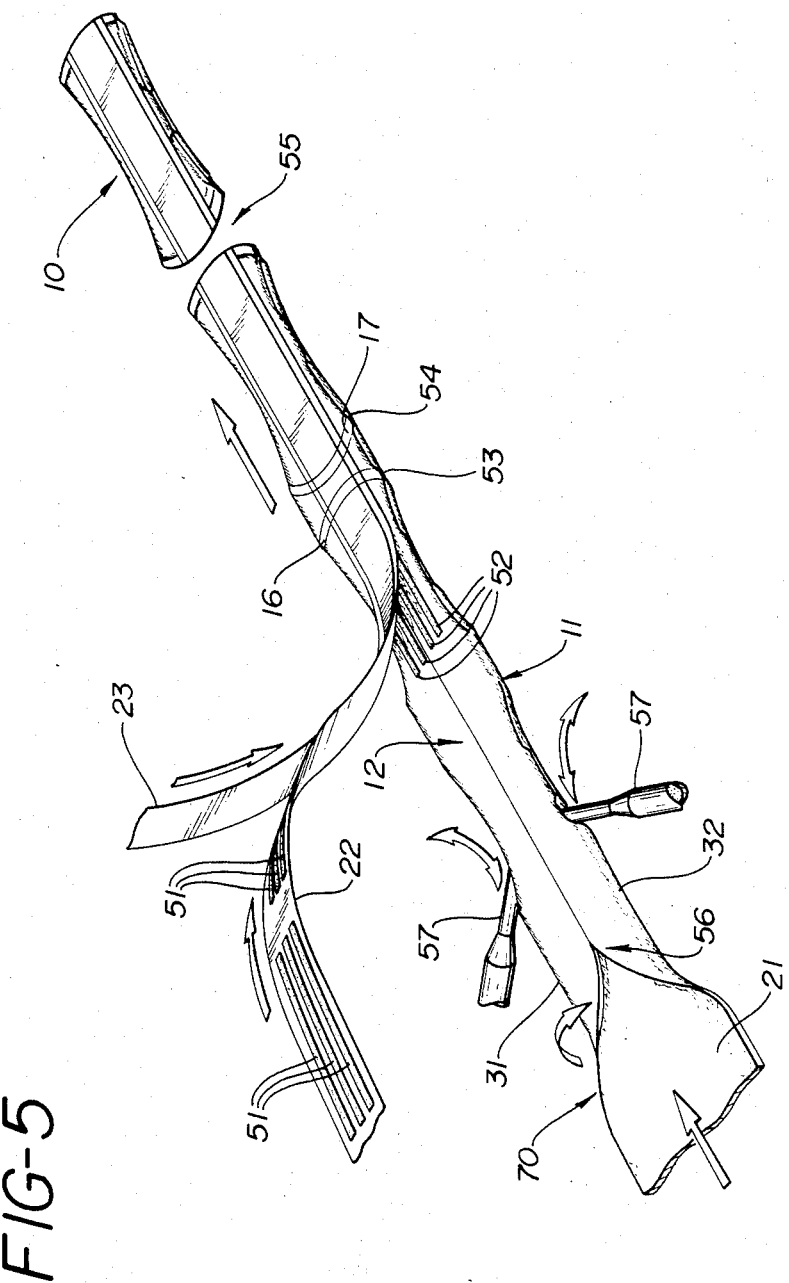

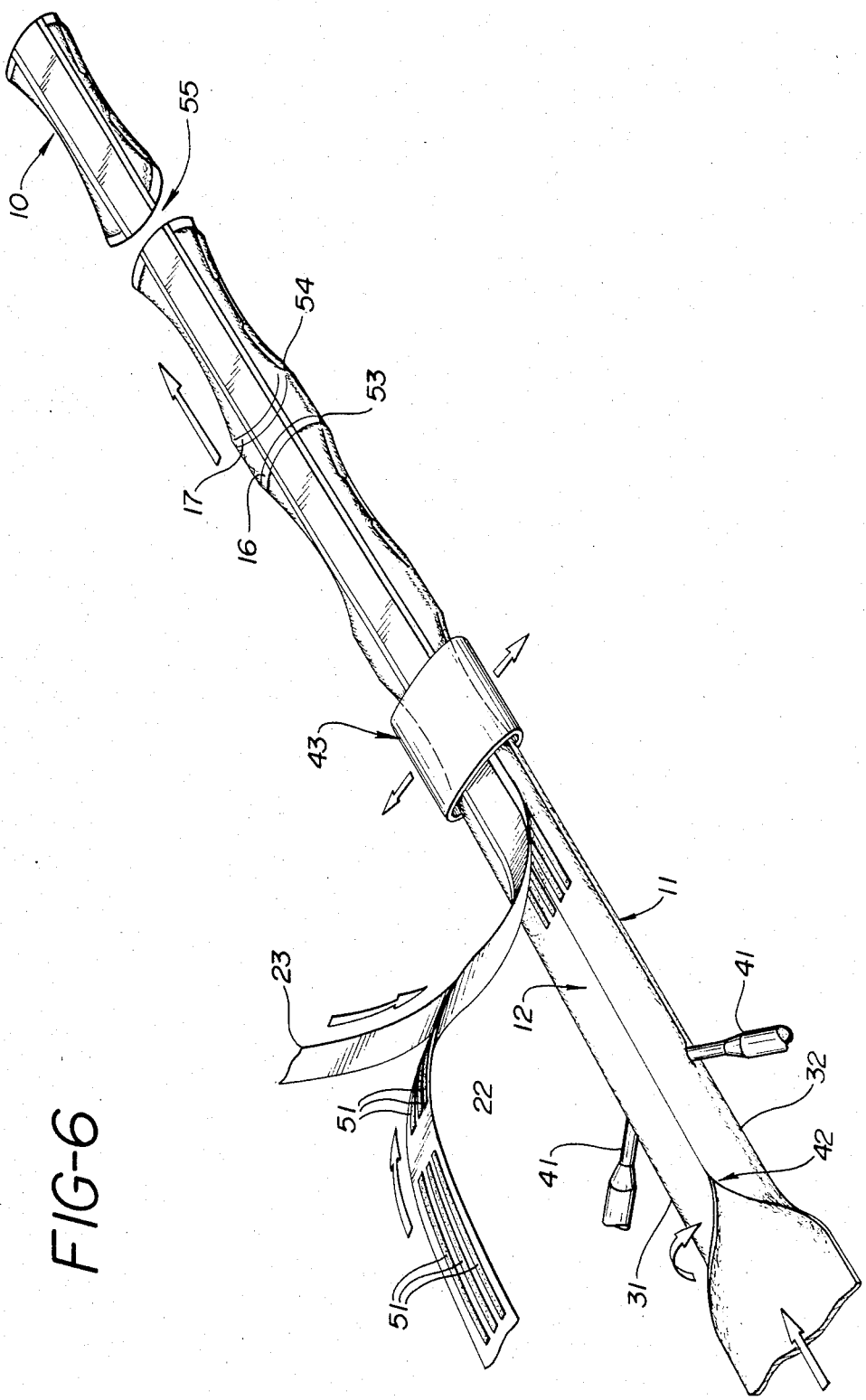

SMOOTH-EDGED CONTOURED SANITARY NAPKIN

BACKGROUND OF THE INVENTION

This invention relates to body contoured sanitary napkins and particularly those which are intended to fit within the crotch portion of an undergarment and protect the garment from body exudates.

The term "napkin" as used herein is intended to encompass nether garment liners such as sanitary napkins and panty shields and more specifically to such products which employ adhesive means for attaching the product to the crotch portion of a nether garment when in use. Such products are provided to absorb and retain body fluids and to protect the nether garment from staining and soiling. It is known in the art to provide absorbent liners comprising an absorbent body having midgarment and body facing major surfaces and provided with pressure-sensitive adhesive means on the garment facing surface for adherence of the product to a nether garment. Generally these liners are provided with a protective release strip overlying the pressure-sensitive element and protecting it from dirt and unintentional adhesion when packaged, stored, and handled prior to use. At the time of use, the strip is peeled from the adhesive means and the product is positioned and adhered to the undergarment. After use, the product is peeled from the undergargment and disposed of.

There are body-contoured sanitary napkins on the market, generally having an "hourglass" shape. However, these commercial products are all constructed by means of a die cutting process so that the product edges tend to be harsh, which may lead to discomfort in use.

There are also numerous products on the market which are "C"-folded so that they possess smooth longitudinal edges, but lack body-contoured shaping. Such prior napkins are disclosed in U.S. Pat. Nos. 4,518,451; 4,023,570 and 4,023,571.

It will thus be seen that known body-contoured sanitary napkins may lead to chafing and discomfort in use; whereas known "C"-folded napkins, although possessing smooth edges, do not conform particularly well to the perineal area of the female body and are thus less comfortable than those which are more body-conforming.

U.S. Pat. Nos. 2,918,065; 3,076,459, and 3,076,460 disclose means for pleating the tab ends of sanitary napkins. However, there is no disclosure in any of said patents concerning the presently claimed method of forming tucks substantially at the midpoint of the longitudinal edges of the napkin.

Accordingly, it is an object of the present invention to produce a "C"-folded napkin with smooth edges and which is nevertheless body contoured. Such achievement is unexpected since "C"-folding and shaping have heretofore been considered to be mutually exclusive.

SUMMARY OF THE INVENTION

In accordance with the objects and principles of the present invention, there is provided a "C"-folded absorbent body useful for a sanitary napkin which while maintaining all the benefits of the smooth edges of a "C"-fold, also provides the advantage of body contoured edges.

The term "C"-fold absorbent body as used herein, means a sheet of absorbent material which is longitudinally divided by two essentially parallel fold lines into a central panel and two side panels. The side panels are folded onto a first surface of the central panel along the fold lines to create a double thickness absorbent body. The folded-over edges are generally smooth and rounded to provide the desired comfort in use. Depending on the relative widths of the side panels and the central panel, the edges of the side panels may be spaced apart on the first surface, may abut or may even overlap. In one extreme, butting panels may be joined so as to form a flat tube. It is preferred, when employed as an absorbent element is a product such as a sanitary napkin, that the "C"-folded absorbent body be utilized so that the central panel is on the body facing side of the product and the folded panels face toward the garment facing side of the product.

A tuck is formed and securely held in place in at least one of the longitudinal folded-over edges of the absorbent body. The tuck is located preferable at the midpoint of the longitudinal edge of the absorbent body. However, the tuck may be located such that it is displaced from each end of the edge of the absorbent body, a distance of at least one-fifth of the length of the one edge, thus providing a concave contour thereto. Most preferably, a tuck is formed in each longitudinal edge of the absorbent body so as to provide an "hourglass" shape thereto. Each tuck is preferably held firmly in place by means of an adhesive although other methods of fixing the tucks in place may be utilized, such as sonic or heat bonding in the instance wherein the absorbent body comprises a thermoplastic material.

When the absorbent body is employed in a sanitary napkin, a fluid impervious layer overlies the garment facing surface of the absorbent body and securing means are also preferably provided for securing the garment facing surface of the napkin to the interior of the crotch portion of a nether garment.

The present invention also relates to a method of manufacturing a smooth edged, contoured, absorbent body useful for an absorbent napkin comprising passing a continuous elongated sheet of absorbent material to an assembly line; "C"-folding the sheet so as to form two substantially parallel longitudinal folded-over edges on either side of a major surface which is adapted for facing the body of a wearer; and tucking at least one of the longitudinal folded-over edges intermittently so as to produce intermittent concave contours in at least one edge of the absorbent body when said absorbent body is viewed in plan. Each tuck is securely fixed in place, preferably by means of an adhesive, and thereafter the continuous sheet is cut into separate individual napkins such that each tuck is displaced from each end of the longitudinal edge of the individual napkin, a distance of at least one-fifth of the length of the edge. A modification of the process of the present invention comprises wrapping an additional absorbent insert within the elongated sheet of absorbent material prior to the "C"-folding step.

BRIEF DESCRIPTION OF THE DRAWINGS

The invention will be better understood by consideration of the following description, taken together with the appended drawings in which:

FIG. 3A is a transverse, cross-sectional view of the napkin of FIG. 1, taken through lines 3—3 of FIG. 1, in the instance wherein the cover material has a moderate degree of flexural resistance;

FIG. 3B is a transverse, cross-sectional view of the napkin of FIG. 1, taken through lines 3—3 of FIG. 1, in the instance wherein the cover material has a low degree of flexural resistance;

FIG. 4 is a transverse, cross-sectional view of the napkin of FIG. 1, taken through lines 3—3 of FIG. 1, there being an additional absorbent insert enclosed within the cover material;

FIG. 4A is a plan view of an embodiment of the napkin of the invention, there being an additional hourglass shaped absorbent insert wrapped within the cover material;

FIG. 4B is a plan view of a further embodiment of the napkin of the invention, there being an additional, rectangular shaped absorbent insert wrapped within the cover material;

FIG. 5 is a schematic diagram of a process for manufacturing the napkin of the invention;

FIG. 6 is a schematic diagram of an alternative process for manufacturing the napkin of the invention.

DETAILED DESCRIPTION OF THE INVENTION

Figure 1:
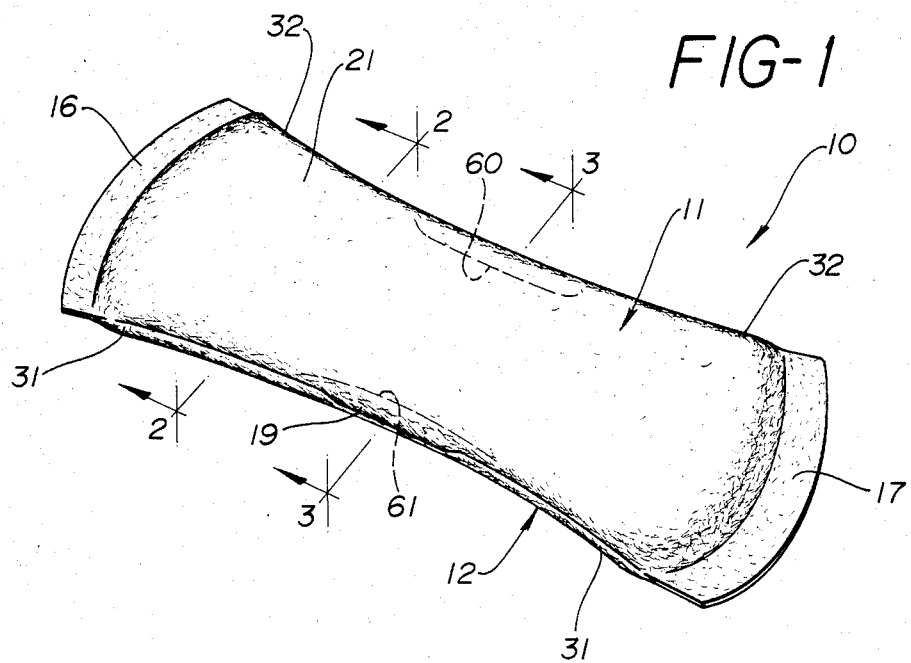
FIG. 1 is a perspective view of the absorbent napkin of this invention.

The sanitary napkin of the invention is shown in FIGS. 1, 2, 3, 3A, 3B, 4 and 4B of the accompanying drawings. FIG. 1 is a perspective view of napkin (10). Napkin (10) comprises a body facing, body fluid pervious side (11) and a garment facing, body fluid impervious side (12). The body facing side of the napkin consists of a sheet (21) which has been "C"-folded at edges (31) and (32).

Affixed to the garment facing side of the "C"-folded sheet is a layer of body fluid impervious material (22) provided to act as a barrier to body fluids and prevent the "strike through"of such fluids onto the undergarment of the wearer. This layer may comprise any thin flexible body fluid impermeable material such as, for example, a polymeric film, e.g., polyethylene, polypropylene, cellophane or even a normally fluid pervious material that has been treated to be impervious such as impregnated fluid repellant paper. As is illustrated in FIGS. 5 and 6 of the drawings the body fluid impervious layer 22 is affixed to the garment facing side of the "C"-folded sheet by means of a plurality of longitudinally extending lines of adhesive 52. Disposed on the garment facing surface of the impervious layer 22 are longitudinally extending pressure sensitive adhesive elements 51 providing for attaching the napkin to the crotch portion of an undergarment. While such adhesive elements are illustrated (in FIG. 5) in the form of longitudinally extending lines, it will be understood that various patterns such as spots or transverse lines will be suitable.

The adhesive employed may be any of the large number of pressure-sensitive adhesives available on the market, including for example, the water based pressure-sensitive adhesives such as the acrylate adhesives e.g., vinyl acetate-2 ethyl hexyl acetate copolymer which is generally combined with tackifiers such as ethylene amine. Alternatively, the adhesive may comprise the rapid-setting thermoplastic (hot melt) adhesives such as block copolymers exemplified by the A-B-A block copolymers wherein the A end block is polystyrene and the midblock is polyolefin copolymer such as poly (ethylene) poly(butylene)copolymer. The adhesive element may also comprise a double faced tape.

Overlying the adhesive elements (51) is a protective release strip (23) which is provided to protect the adhesive elements (51) from dirt and unintended adhesion prior to use. The strip (23) may be constructed of any suitable sheet-like material which adheres with sufficient tenacity to the adhesive element to remain in place prior to use but which can be readily removed when the napkin is to be used. A particularly useful material is a semi-bleached kraft paper, the adhesive contacting side of which has been silicone treated to provide easy release from the adhesive elements (51).

Figure 3:
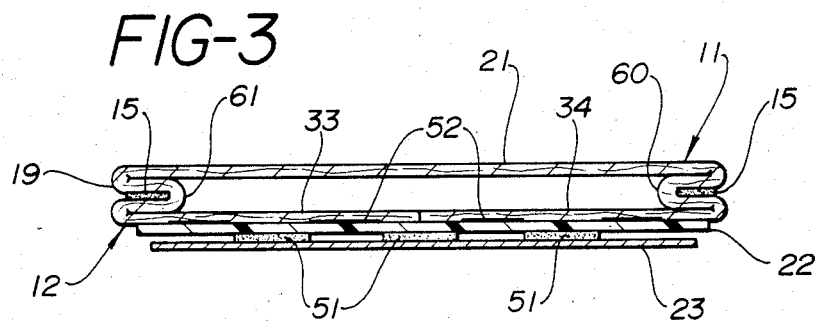
FIG. 3 is a transverse, cross-sectional view of the napkin of FIG. 1, taken through lines 3—3 of FIG. 1, in the instance wherein the cover material has a high degree of flexural resistance.

As can be clearly seen from FIGS. 3, 3A, 3B, and 4, of the accompanying drawings, which are transverse cross-sectional views taken through line 3—3 of FIG. 1, tucks (60), (61) have been formed at the midpoints of edges 31 and 32 of the napkin (10) so that said edges have assumed an hourglass shape when the napkin is viewed in plan. The tucked-in portion (60) and (61) of edges (31) and (32) respectively are shown in FIGS. 1 and 3 of the drawings. Hot melt adhesive (15) has been applied to the tucks (60) and (61) so as to hold them securely in position. Although tucks (60) and (61) are preferably located at the midpoint of each edge they may nevertheless be located so that each tuck is displaced from each end of each edge of the napkin a distance of at least one-fifth of the length of such edge.

Figure 2:
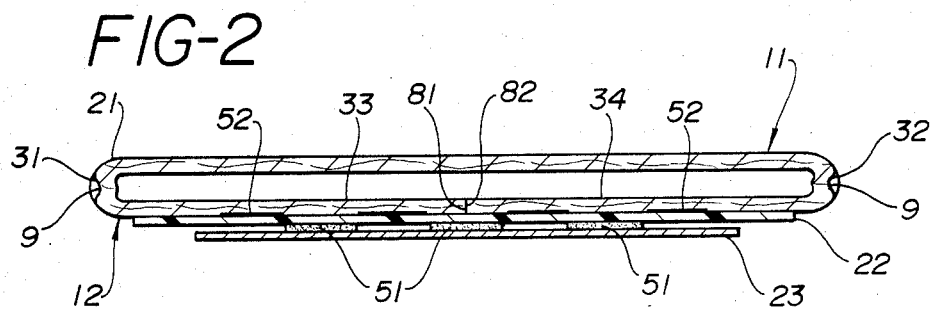
FIG. 2 is a transverse, cross-sectional view of the napkin of FIG. 1, taken through lines 2—2 of FIG. 1.

A cross-sectional view of the napkin of FIG. 1, taken through lines 2—2 thereof is shown in FIG. 2 of the drawings. It will be noted that at line 2—2, the depths of the tucks (60) and (61) are very slight.

The ends of the napkin (10) are shown as having been sealed by crimping at (16) and (17), in FIG. 1 of the drawings. It will be noted that there are no tucks present at the ends of the napkin.

If desired, a planar absorbent insert (90) or (92), shown in FIGS. 4, 4A and 4B of the drawings, may be incorporated into the "C"-folded napkin. A method of incorporated such as absorbent insert is described in detail in U.S. Pat. No. 4,518,451, which is incorporated herein by reference. Briefly, U.S. Pat. No. 4,518,451 discloses a method wherein, prior to the "C"-folding step, an additional elongated absorbent insert, having a width no greater than that of the major surface of the sheet which is adapted to contact the body of the wearer, is superimposed on a central longitudinal portion of the sheet opposite to the body facing major surface thereof, with the sheet extending transversely on either longitudinal side of the insert, so that after the "C"-folding step, the insert is wrapped within said sheet.

Although U.S. Pat. No. 4,518,451 only discloses the incorporation of a substantially rectangular shaped insert (such as insert (92) shown in FIG. 4B of the present drawings), an hourglass shaped insert, such as insert (90) shown in FIG. 4A of the present drawings, may easily be incorporated into the napkin in accordance with the method shown in U.S. Pat. No. 4,518,451, simply by appropriately preshaping the insert in a manner well known in the art. It will be noted from FIG. 4 of the present drawings that the width of the insert (90) or (92) at the center thereof is chosen so that it is approximately the same as the distance between the tucked-in portions (60) and (61) of edges 31 and 32 as shown in FIG. 3 of the drawings.

The absorbent sheet (21) utilized in accordance with the present invention may comprise any of the absorbent, flexible materials now used for producing body fluid absorbing products. Such sheet should have structural integrity and should have a minimum thickness of about 0.01 cm. and preferably at least 0.05 cm. thick. Any insert which may be incorporated into the napkin should likewise be constructed of one of such absorbent materials for absorbing body fluids and may in fact be the same material as that of the sheet (21). The thickness of the absorbent insert may vary widely, depending upon the extent of absorbency desired.

The choice of materials for the absorbent sheet (21), as well as any insert may vary widely.

The materials cited in U.S. Pat. No. 4,023,571 and U.S. Pat. No. 4,023,570 may be suitable. As described in these patents, a particularly useful material is the lofty and soft nonwoven, through bonded fabric described in U.S. Pat. No. 3,663,238. This fabric consists essentially of a mixture of approximately 25% by weight, of long (about 2.9 cms) rayon fibers and about 75% by weight of short (about 0.2 cms) wood pulp fibers and has a water dispersable binder applied throughout in an amount of between about 1% and about 30% of the weight of the fibers on a dry basis. The binders of choice are the self-curing acrylic latex type, the urethane type, or other similar binders. The fabric has a weight of less than about 8 ounces per square yard and a density of about 0.15 to about 0.05 grams per cc.

Another particularly suitable absorbent material for use as both the absorbent sheet and any insert of this invention is a low density, highly absorbent, thermal bonded nonwoven fabric comprising a mixture of absorbent fibers and staple length polyester/polyethylene conjugate fibers. The absorbent fibers are preferably wood pulp or other cellulosic fibers which may have been treated to enhance absorbency. The conjugate fibers are fibers which comprise a polyester core surrounded by a sheath of polyethylene.

Preferably, the conjugate fibers employ high density polyethylene, that is, linear polyethylene that has a density of at least 0.94, and a Melt Index (as determined by ASTMD-1238E method, employing the parameters of 190° C., and 2160 gm) of greater than 1, preferably greater than about 10, and more preferably from about 20 to about 50. The fibers may comprise from about 40 to 60 percent, by weight polyester and preferably from 45 to 55 weight percent polyester, the remainder being polyethylene. Such fibers may be used in deniers of from 1 to about 6 and may be from about ½ inch to about 3 or 4 inches long. Preferably the fabric comprises outer layers of heat fusible fibers having the mixture of wood pulp and conjugate fibers sandwiched therebetween. Such outer layers may consist of the conjugate fibers or may in fact be any heat-fusible materials such as polypropylene fibers, for example. The fabric is stabilized by applying heat thereto under essentially zero pressure whereby thermal bonding takes place without destroying the integrity of the fibers and low density is maintained. Typically, the bulk density of such fabrics is less than about 0.15 grams per cubic centimeter.

An example of the above is a product which is produced by employing for both the sheet and the optional insert material a thermal bonded absorbent fabric comprising, overall, 54% by weight of wood pump fibers and 46% by weight of conjugate fibers having a polyester core and a high density polyethylene sheath. The conjugate fibers have a staple length of 3.81 cm. and a denier of 3.0. The materials are so distributed as to provide a pulp/conjugate fiber mixture sandwiched between two veneers of conjugate fibers, the veneers having basis weights of 0.27 oz/yd$^2$ and 0.37 oz/yd$^2$, the heavier veneer ultimately being employed on the body facing side of the product. The fabric is stabilized by passing hot air through the fibers and thereby melting the high density polyethylene which bonds the fibers together upon cooling. The overall fabric has a basis weight of 2.5 oz/yd$^2$, is about 0.165 cm. thick and has machine direction and cross direction tensile strength of 5.3 and 1.1 pounds/inch of width, respectively. The fabric is capable of holding about 17 times its own weight of distilled water.

In FIG. 5 there is illustrated a schematic assembly line for producing the product of this invention. As is illustrated, an elongated absorbent sheet (21) comprising absorbent material is passed to the assembly line, after having been "C"-folded as shown at (70).

A sub-assembly consisting of a polyethylene film barrier (22), adhered to a release strip (23), by means of adhesive elements (51) is laminated by means of adhesive (52) to the second major surface (12) of sheet (21). The "C"-folded web is tucked intermittently by means of pivoting hot melt nozzles (57) with simultaneous hot melt adhesive application. In this manner, tucks are formed intermittently in both longitudinal edges (31) and (32) of the assembly. The tucks are displaced from the succeeding tucks a distance such that, after the assembly is cut into individual units (10), the central portion of each unit will be formed with one tuck in each edge.

After the intermittent tucking step, the assembly is passed to a crimping station (53, 54) for crimping the assembly in portions 16 and 17 respectively corresponding to the ends of the finished unit napkin (10) in order to close these ends and the product is next cut at a cutting station (55) utilizing an orbital knife and separated into the individual napkins (10). The adhesive used for holding the tucks in place is preferably a quick setting type such as atactic polypropylene hot melt adhesive sold by Eastman Chemical as EASTOBOND A337S. The napkin (10) prepared by the aforementioned procedure is hourglass shaped and has smooth, "C"-folded edges.

An alternative method of manufacturing the product of the present invention is illustrated in FIG. 6 of the drawings. In accordance with this method, the assembly is "C"-folded and laminated with the sub-assembly (22), (23) in a similar manner to that described with respect to FIG. 5 of the drawings. In this alternative method, the hot melt nozzles (41) do not pivot, but are pressed into the longitudinal edges of the assembly so as to produce a continuous tuck in both of said edges. However, quick-setting adhesive is nevertheless applied intermittently on those portions which will subsequently constitute the mid-point of the resulting unit napkin. The assembly is then passed through a station (43) in which a slight negative pressure is applied to the longitudinal edges (31) and (32) of the tucked assembly. This results in the assembly becoming untucked only in those areas which lack adhesive. The web is then crimped and cut, forming tab ends in the identical manner to that shown in connection with FIG. 5 of the drawings. Similarly, the end result is an hourglass shaped napkin possessing smooth, "C"-folded edges.

Although the tucks are preferably fixed in place by means of an adhesive, if the sheet (21) is heat sealable the tucks may alternatively be held in place by means of thermal bonding.

With reference to FIG. 2 of the drawings, it will be seen that folded over portions (33) and (34) of the absorbent sheet almost about at edges (81) and (82) respectively. However, it is obvious that even if a wide gap existed between edges (81) and (82), or even if said edges (81) and (82) were to overlap or to be integrally joined together so as to constitute a closed tube, the napkin of the invention would function just as effectively as it does in the preferred embodiment. Similarly, FIG. 2 of the drawings shows an absorbent body which is folded in the form of a "C", with the bight of said "C" constituting the body facing major surface. However, the present invention would also be effective if the bight of the "C" were to constitute the garment facing surface.

I claim:

1. In a "C"-folded absorbent body having folded over longitudinal edges, a tuck being formed and securely held in place in at least one of said longitudinal edges, said tuck being displaced from each end of said one edge a distance of at least one fifth of the length of said one edge, thus providing a concave contour to said one edge when said absorbent body is viewed in plan.

2. A smooth edged, hourglass shaped, absorbent napkin, comprising: an elongated absorbent body having major surface adapted for facing the body of a wearer and an opposite gargment facing major surface; said absorbent body having transverse ends and being "C"-folded over longitudinal edges, securing means for securing said napkin to the interior of the crotch portion of a nether garment; a tuck being formed and securely held in place in each of said longitudinal edges of said absorbent body, each of said tucks being displaced from the ends of the edge in which it is formed, a distance of at least one fifth of the length of said edge, thus providing an hourglass shaped contour to said napkin when it is viewed in plan.

3. The napkin of claim 2, in which the bight of said "C" fold constitutes said body facing major surface.

4. The napkin of claim 2, in which the bight of said "C" fold is opposite to said body facing major surface.

5. The napkin of claim 2, in which said absorbent body comprises a tube.

6. The napkin of claim 2, in which said securing means comprises a pressure sensitive adhesive element disposed upon a portion of said napkin opposite to said body facing major surface, there being a removable protective release strip overlying said pressure sensitive adhesive element.

7. The napkin of claim 2, wherein said absorbent body comprises an absorbent material having a fluid impervious layer overlying and adhered to said garment facing major surface.

8. The napkin of claim 2, wherein said absorbent body is folded around an absorbent insert.

9. The napkin of claim 2, wherein said tucks are formed substantially in the middle of each of said longitudinal edges.

10. The napkin of claim 2, wherein each tuck is held in place by means of an adhesive.

11. The napkin of claim 2, wherein said absorbent body is formed of thermoplastic material, and each tuck is held in place by means of sonic or heat bonding.

12. A method of manufacturing a smooth edged, contoured absorbent body useful for a sanitary napkin, said absorbent body having a major surface adapted for facing the body of a wearer and an opposite garment facing major surface, said absorbent body having transverse ends and being "C"-folded over longitudinal edges, said method comprising: passing a continuous layer of absorbent material to an assembly line; folding said layer in the form of a "C" so as to form two substantially parallel longitudinal edges on either side of said body facing major surface of said layer; tucking at least one of said longitudinal edges intermittently so as to produce intermittent concave contours in said one edge when said absorbent body is viewed in plan, securely fixing said tucks in place; and cutting said continuous sheet into separate individual napkins, each having a single tuck in said one longitudinal edge, said tuck being displaced from each end of said one longitudinal edge of each individual napkin a distance of at least one fifth of the length of said one edge of each napkin.

13. The method of claim 12, wherein an elongated fluid impervious web is laminated to said garment facing major surface.

14. The method of claim 12, in which both of said longitudinal edges are subjected to said tucking steps.

15. The method of claim 14, wherein prior to said folding step, an additional elongated absorbent insert, having a width slightly less than that of said body facing major surface of said layer, is superimposed on a central longitudinal portion of said layer opposite to said body facing major surface of said layer, with said layer extending transversely on either longitudinal side of said insert, so that after the folding step, said insert is wrapped within said layer.

16. The method of claim 14, wherein each end of each individual napkin is closed by means of crimping.

17. The method of claim 14, in which adhesive is applied to each tuck to fix it in place.

18. The method of claim 14, wherein said layer is thermoplastic and each tuck is fixed in place by means of heat bonding.

19. A modification of the method of claim 14, which comprises forming a continuous longitudinal tuck in each of said longitudinal edges; applying adhesive intermittently along said continuous tuck and thereafter applying slight negative pressure along said edges so that said edges become untucked in those areas which lack adhesive.

* * * * *